(12) United States Patent
Xin

(10) Patent No.: US 10,590,178 B2
(45) Date of Patent: Mar. 17, 2020

(54) CHIMERIC VACCINE AGAINST FUNGAL INFECTIONS

(71) Applicant: Hong Xin, New Orleans, LA (US)

(72) Inventor: Hong Xin, New Orleans, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 127 days.

(21) Appl. No.: 15/320,225

(22) PCT Filed: Jun. 19, 2015

(86) PCT No.: PCT/US2015/036593
§ 371 (c)(1),
(2) Date: Dec. 19, 2016

(87) PCT Pub. No.: WO2015/200107
PCT Pub. Date: Dec. 30, 2015

(65) Prior Publication Data
US 2017/0137476 A1 May 18, 2017

Related U.S. Application Data

(60) Provisional application No. 62/016,693, filed on Jun. 25, 2014.

(51) Int. Cl.
| | | |
|---|---|---|
| *C07K 14/40* | (2006.01) | |
| *A61K 39/00* | (2006.01) | |
| *C07K 16/14* | (2006.01) | |
| *A61K 39/395* | (2006.01) | |

(52) U.S. Cl.
CPC .......... *C07K 14/40* (2013.01); *A61K 39/0002* (2013.01); *A61K 39/39575* (2013.01); *C07K 16/14* (2013.01); *A61K 2039/505* (2013.01); *A61K 2039/507* (2013.01); *A61K 2039/55505* (2013.01); *A61K 2039/575* (2013.01); *A61K 2039/6037* (2013.01); *C07K 2317/24* (2013.01); *C07K 2319/40* (2013.01); *C07K 2319/55* (2013.01)

(58) Field of Classification Search
None
See application file for complete search history.

(56) References Cited

U.S. PATENT DOCUMENTS

| | | | |
|---|---|---|---|
| 6,583,275 B1 | 6/2003 | Doucette-Stamm et al. | 536/23.1 |
| 7,241,613 B1 | 7/2007 | Willins et al. | 435/255.4 |
| 8,541,008 B2 | 9/2013 | Edwards, Jr. et al. | 424/274.1 |
| 2013/0004485 A1 | 1/2013 | Bansal | 424/133.1 |
| 2014/0037641 A1 | 2/2014 | Cutler et al. | 424/139.1 |

FOREIGN PATENT DOCUMENTS

WO    WO 2012/145666    10/2012

OTHER PUBLICATIONS

Xin, H., "Double Chimeric Peptide Vaccine and Monoclonal Antibodies that Protect Against Disseminated Candidasis," Journal of Vaccines & Vaccination, vol. 5, No. 4, pp. 1-8 (2014).
Xin, H. et al., "Synthetic Glycopeptide Vaccines Combining β-Mannan and Peptide Epitopes Induce Protection Against Candidiasis," Proc. Natl. Acad. Sci. USA, vol. 105, pp. 13526-13531 (2008).
Xin, H. et al., "Vaccine and Monoclonal Antibody that Enhance Mouse Resistance to Candidiasis," Clin. Vaccine Immunol., vol. 18, pp. 1656-1667 (2011).
Xin, H. et al., "Self-Adjuvanting Glycopeptide Conjugate Vaccine Against Disseminated Candidiasis," PloS One 7.

*Primary Examiner* — Robert A Zeman
(74) *Attorney, Agent, or Firm* — John H. Runnels

(57) ABSTRACT

Chimeric double peptide vaccines are disclosed, useful for inducing active immunity against *Candida* fungal infections. The chimeric peptide comprises an Fba peptide and an Met6 peptide, covalently linked to one another, with or without an intermediate linker. Fba and Met6 are cell surface components of *Candida*. When used as a vaccine, the chimeric double peptide vaccine induces stronger protective immunity against fungal infection than does the Fba peptide alone, or the Met6 peptide alone, or a mixture (not covalently linked) of the two peptides.

6 Claims, 10 Drawing Sheets

Specification includes a Sequence Listing.

SEQUENCE LISTING

<160> NUMBER OF SEQ ID NOS: 26

<210> SEQ ID NO 1
<211> LENGTH: 14
<212> TYPE: PRT
<213> ORGANISM: Artificial sequence
<220> FEATURE:
<223> OTHER INFORMATION: Fba peptide

<400> SEQUENCE: 1

Tyr Gly Lys Asp Val Lys Asp Leu Phe Asp Tyr Ala Gln Glu
1               5                   10

<210> SEQ ID NO 2
<211> LENGTH: 14
<212> TYPE: PRT
<213> ORGANISM: Artificial sequence
<220> FEATURE:
<223> OTHER INFORMATION: Met6 peptide

<400> SEQUENCE: 2

Pro Arg Ile Gly Gly Gln Arg Glu Leu Lys Lys Ile Thr Glu
1               5                   10

<210> SEQ ID NO 3
<211> LENGTH: 30
<212> TYPE: PRT
<213> ORGANISM: Artificial sequence
<220> FEATURE:
<223> OTHER INFORMATION: Fba-KK-Met6 Peptide

<400> SEQUENCE: 3

Tyr Gly Lys Asp Val Lys Asp Leu Phe Asp Tyr Ala Gln Glu Lys Lys
1               5                   10                  15

Pro Arg Ile Gly Gly Gln Arg Glu Leu Lys Lys Ile Thr Glu
            20                  25                  30

<210> SEQ ID NO 4
<211> LENGTH: 30
<212> TYPE: PRT
<213> ORGANISM: Artificial sequence
<220> FEATURE:
<223> OTHER INFORMATION: Met6-KK-Fba peptide

<400> SEQUENCE: 4

Tyr Gly Lys Asp Val Lys Asp Leu Phe Asp Tyr Ala Gln Glu Lys Lys
1               5                   10                  15

Pro Arg Ile Gly Gly Gln Arg Glu Leu Lys Lys Ile Thr Glu
            20                  25                  30

<210> SEQ ID NO 5
<211> LENGTH: 34
<212> TYPE: PRT
<213> ORGANISM: Artificial sequence
<220> FEATURE:
<223> OTHER INFORMATION: Fba-GGSSGG-Met6 Peptide

<400> SEQUENCE: 5

Tyr Gly Lys Asp Val Lys Asp Leu Phe Asp Tyr Ala Gln Glu Gly Gly
1               5                   10                  15

Ser Ser Gly Gly Pro Arg Ile Gly Gly Gln Arg Glu Leu Lys Lys Ile
            20                  25                  30

Thr Glu

```
<210> SEQ ID NO 6
<211> LENGTH: 30
<212> TYPE: PRT
<213> ORGANISM: Artificial sequence
<220> FEATURE:
<223> OTHER INFORMATION: Met6-GG-Fba peptide

<400> SEQUENCE: 6

Pro Arg Ile Gly Gly Gln Arg Glu Leu Lys Lys Ile Thr Glu Gly Gly
1               5                   10                  15

Tyr Gly Lys Asp Val Lys Asp Leu Phe Asp Tyr Ala Gln Glu
            20                  25                  30

<210> SEQ ID NO 7
<211> LENGTH: 30
<212> TYPE: PRT
<213> ORGANISM: Artificial sequence
<220> FEATURE:
<223> OTHER INFORMATION: Fba-PP-Met6 peptide

<400> SEQUENCE: 7

Tyr Gly Lys Asp Val Lys Asp Leu Phe Asp Tyr Ala Gln Glu Pro Pro
1               5                   10                  15

Pro Arg Ile Gly Gly Gln Arg Glu Leu Lys Lys Ile Thr Glu
            20                  25                  30

<210> SEQ ID NO 8
<211> LENGTH: 30
<212> TYPE: PRT
<213> ORGANISM: Artificial sequence
<220> FEATURE:
<221> NAME/KEY: misc_feature
<222> LOCATION: (1)..(1)
<223> OTHER INFORMATION: Fba-KK-Met6 peptide. Xaa at position 1 is
      methylated Tyrosine.
<220> FEATURE:
<223> OTHER INFORMATION: Predicted synthetic sequence.

<400> SEQUENCE: 8

Xaa Gly Lys Asp Val Lys Asp Leu Phe Asp Tyr Ala Gln Glu Lys Lys
1               5                   10                  15

Pro Arg Ile Gly Gly Gln Arg Glu Leu Lys Lys Ile Thr Glu
            20                  25                  30

<210> SEQ ID NO 9
<211> LENGTH: 30
<212> TYPE: PRT
<213> ORGANISM: Artificial sequence
<220> FEATURE:
<221> NAME/KEY: misc_feature
<222> LOCATION: (2)..(2)
<223> OTHER INFORMATION: Fba-KK-Met6 peptide. Xaa at position 2 is
      methylated Glycine.
<220> FEATURE:
<223> OTHER INFORMATION: Predicted synthetic sequence.

<400> SEQUENCE: 9

Tyr Xaa Lys Asp Val Lys Asp Leu Phe Asp Tyr Ala Gln Glu Lys Lys
1               5                   10                  15

Pro Arg Ile Gly Gly Gln Arg Glu Leu Lys Lys Ile Thr Glu
            20                  25                  30

<210> SEQ ID NO 10
<211> LENGTH: 30
<212> TYPE: PRT
<213> ORGANISM: Artificial sequence
<220> FEATURE:
```

```
<221> NAME/KEY: misc_feature
<222> LOCATION: (3)..(3)
<223> OTHER INFORMATION: Fba-KK-Met6 peptide. Xaa at position 3 is
      methylated Lysine.
<220> FEATURE:
<223> OTHER INFORMATION: Predicted synthetic sequence.

<400> SEQUENCE: 10

Tyr Gly Xaa Asp Val Lys Asp Leu Phe Asp Tyr Ala Gln Glu Lys Lys
1               5                   10                  15

Pro Arg Ile Gly Gly Gln Arg Glu Leu Lys Lys Ile Thr Glu
            20                  25                  30

<210> SEQ ID NO 11
<211> LENGTH: 30
<212> TYPE: PRT
<213> ORGANISM: Artificial sequence
<220> FEATURE:
<221> NAME/KEY: misc_feature
<222> LOCATION: (5)..(5)
<223> OTHER INFORMATION: Fba-KK-Met6 peptide. Xaa at position 5 is
      methylated Valine.
<220> FEATURE:
<223> OTHER INFORMATION: Predicted synthetic sequence.

<400> SEQUENCE: 11

Tyr Gly Lys Asp Xaa Lys Asp Leu Phe Asp Tyr Ala Gln Glu Lys Lys
1               5                   10                  15

Pro Arg Ile Gly Gly Gln Arg Glu Leu Lys Lys Ile Thr Glu
            20                  25                  30

<210> SEQ ID NO 12
<211> LENGTH: 30
<212> TYPE: PRT
<213> ORGANISM: Artificial sequence
<220> FEATURE:
<221> NAME/KEY: misc_feature
<222> LOCATION: (6)..(6)
<223> OTHER INFORMATION: Fba-KK-Met6 peptide. Xaa at position 6 is
      methylated Lysine.
<220> FEATURE:
<223> OTHER INFORMATION: Predicted synthetic sequence.

<400> SEQUENCE: 12

Tyr Gly Lys Asp Val Xaa Asp Leu Phe Asp Tyr Ala Gln Glu Lys Lys
1               5                   10                  15

Pro Arg Ile Gly Gly Gln Arg Glu Leu Lys Lys Ile Thr Glu
            20                  25                  30

<210> SEQ ID NO 13
<211> LENGTH: 30
<212> TYPE: PRT
<213> ORGANISM: Artificial sequence
<220> FEATURE:
<221> NAME/KEY: misc_feature
<222> LOCATION: (8)..(8)
<223> OTHER INFORMATION: Fba-KK-Met6 peptide. Xaa at position 8 is
      methylated Leucine.
<220> FEATURE:
<223> OTHER INFORMATION: Predicted synthetic sequence.

<400> SEQUENCE: 13

Tyr Gly Lys Asp Val Lys Asp Xaa Phe Asp Tyr Ala Gln Glu Lys Lys
1               5                   10                  15

Pro Arg Ile Gly Gly Gln Arg Glu Leu Lys Lys Ile Thr Glu
            20                  25                  30
```

<210> SEQ ID NO 14
<211> LENGTH: 30
<212> TYPE: PRT
<213> ORGANISM: Artificial sequence
<220> FEATURE:
<221> NAME/KEY: misc_feature
<222> LOCATION: (9)..(9)
<223> OTHER INFORMATION: Fba-KK-Met6 peptide. Xaa at position 9 is
      methylated Phenylalanine.
<220> FEATURE:
<223> OTHER INFORMATION: Predicted synthetic sequence.

<400> SEQUENCE: 14

Tyr Gly Lys Asp Val Lys Asp Leu Xaa Asp Tyr Ala Gln Glu Lys Lys
1               5                   10                  15

Pro Arg Ile Gly Gly Gln Arg Glu Leu Lys Lys Ile Thr Glu
            20                  25                  30

<210> SEQ ID NO 15
<211> LENGTH: 30
<212> TYPE: PRT
<213> ORGANISM: Artificial sequence
<220> FEATURE:
<221> NAME/KEY: misc_feature
<222> LOCATION: (11)..(11)
<223> OTHER INFORMATION: Fba-KK-Met6 peptide. Xaa at position 11 is
      methylated Tyrosine.
<220> FEATURE:
<223> OTHER INFORMATION: Predicted synthetic sequence.

<400> SEQUENCE: 15

Tyr Gly Lys Asp Val Lys Asp Leu Phe Asp Xaa Ala Gln Glu Lys Lys
1               5                   10                  15

Pro Arg Ile Gly Gly Gln Arg Glu Leu Lys Lys Ile Thr Glu
            20                  25                  30

<210> SEQ ID NO 16
<211> LENGTH: 30
<212> TYPE: PRT
<213> ORGANISM: Artificial sequence
<220> FEATURE:
<221> NAME/KEY: misc_feature
<222> LOCATION: (20)..(20)
<223> OTHER INFORMATION: Fba-KK-Met6 peptide. Xaa at position 20 is
      methylated Glycine.
<220> FEATURE:
<223> OTHER INFORMATION: Predicted synthetic sequence.

<400> SEQUENCE: 16

Tyr Gly Lys Asp Val Lys Asp Leu Phe Asp Tyr Ala Gln Glu Lys Lys
1               5                   10                  15

Pro Arg Ile Xaa Gly Gln Arg Glu Leu Lys Lys Ile Thr Glu
            20                  25                  30

<210> SEQ ID NO 17
<211> LENGTH: 30
<212> TYPE: PRT
<213> ORGANISM: Artificial sequence
<220> FEATURE:
<221> NAME/KEY: misc_feature
<222> LOCATION: (25)..(25)
<223> OTHER INFORMATION: Fba-KK-Met6 peptide. Xaa at position 25 is
      methylated Leucine.
<220> FEATURE:
<223> OTHER INFORMATION: Predicted synthetic sequence.

<400> SEQUENCE: 17

Tyr Gly Lys Asp Val Lys Asp Leu Phe Asp Tyr Ala Gln Glu Lys Lys
1               5                   10                  15

Pro Arg Ile Gly Gly Gln Arg Glu Xaa Lys Lys Ile Thr Glu
            20                  25                  30

<210> SEQ ID NO 18
<211> LENGTH: 30
<212> TYPE: PRT
<213> ORGANISM: Artificial sequence
<220> FEATURE:
<221> NAME/KEY: misc_feature
<222> LOCATION: (26)..(26)
<223> OTHER INFORMATION: Fba-KK-Met6 peptide. Xaa at position 26 is
      methylated Lysine.
<220> FEATURE:
<223> OTHER INFORMATION: Predicted synthetic sequence.

<400> SEQUENCE: 18

Tyr Gly Lys Asp Val Lys Asp Leu Phe Asp Tyr Ala Gln Glu Lys Lys
1               5                   10                  15

Pro Arg Ile Gly Gly Gln Arg Glu Leu Xaa Lys Ile Thr Glu
            20                  25                  30

<210> SEQ ID NO 19
<211> LENGTH: 30
<212> TYPE: PRT
<213> ORGANISM: Artificial sequence
<220> FEATURE:
<221> NAME/KEY: misc_feature
<222> LOCATION: (27)..(27)
<223> OTHER INFORMATION: Fba-KK-Met6 peptide. Xaa at position 27 is
      methylated Lysine.
<220> FEATURE:
<223> OTHER INFORMATION: Predicted synthetic sequence.

<400> SEQUENCE: 19

Tyr Gly Lys Asp Val Lys Asp Leu Phe Asp Tyr Ala Gln Glu Lys Lys
1               5                   10                  15

Pro Arg Ile Gly Gly Gln Arg Glu Leu Lys Xaa Ile Thr Glu
            20                  25                  30

<210> SEQ ID NO 20
<211> LENGTH: 30
<212> TYPE: PRT
<213> ORGANISM: Artificial sequence
<220> FEATURE:
<221> NAME/KEY: misc_feature
<222> LOCATION: (1)..(1)
<223> OTHER INFORMATION: Fba-KK-Met6 peptide. Xaa at position 1 is
      methylated Tyrosine.
<220> FEATURE:
<223> OTHER INFORMATION: Predicted synthetic sequence.
<220> FEATURE:
<221> NAME/KEY: misc_feature
<222> LOCATION: (8)..(8)
<223> OTHER INFORMATION: Fba-KK-Met6 peptide. Xaa at position 8 is
      methylated Leucine.
<220> FEATURE:
<223> OTHER INFORMATION: Predicted synthetic sequence.

<400> SEQUENCE: 20

Xaa Gly Lys Asp Val Lys Asp Xaa Phe Asp Tyr Ala Gln Glu Lys Lys
1               5                   10                  15

Pro Arg Ile Gly Gly Gln Arg Glu Leu Lys Lys Ile Thr Glu
            20                  25                  30

<210> SEQ ID NO 21
<211> LENGTH: 30
<212> TYPE: PRT
<213> ORGANISM: Artificial sequence

```
<220> FEATURE:
<221> NAME/KEY: misc_feature
<222> LOCATION: (5)..(5)
<223> OTHER INFORMATION: Fba-KK-Met6 peptide. Xaa at position 5 is
      methylated Valine.
<220> FEATURE:
<223> OTHER INFORMATION: Predicted synthetic sequence.
<220> FEATURE:
<221> NAME/KEY: misc_feature
<222> LOCATION: (8)..(8)
<223> OTHER INFORMATION: Fba-KK-Met6 peptide. Xaa at position 8 is
      methylated Leucine.
<220> FEATURE:
<223> OTHER INFORMATION: Predicted synthetic sequence.

<400> SEQUENCE: 21

Tyr Gly Lys Asp Xaa Lys Asp Xaa Phe Asp Tyr Ala Gln Glu Lys Lys
1               5                  10                  15

Pro Arg Ile Gly Gly Gln Arg Glu Leu Lys Lys Ile Thr Glu
            20                  25                  30

<210> SEQ ID NO 22
<211> LENGTH: 30
<212> TYPE: PRT
<213> ORGANISM: Artificial sequence
<220> FEATURE:
<221> NAME/KEY: misc_feature
<222> LOCATION: (5)..(5)
<223> OTHER INFORMATION: Fba-KK-Met6 peptide. Xaa at position 5 is
      methylated Valine.
<220> FEATURE:
<223> OTHER INFORMATION: Predicted synthetic sequence.
<220> FEATURE:
<221> NAME/KEY: misc_feature
<222> LOCATION: (25)..(25)
<223> OTHER INFORMATION: Fba-KK-Met6 peptide. Xaa at postion 25 is
      methylated Leucine.
<220> FEATURE:
<223> OTHER INFORMATION: Predicted synthetic sequence.

<400> SEQUENCE: 22

Tyr Gly Lys Asp Xaa Lys Asp Leu Phe Asp Tyr Ala Gln Glu Lys Lys
1               5                  10                  15

Pro Arg Ile Gly Gly Gln Arg Glu Xaa Lys Lys Ile Thr Glu
            20                  25                  30

<210> SEQ ID NO 23
<211> LENGTH: 32
<212> TYPE: PRT
<213> ORGANISM: Artificial sequence
<220> FEATURE:
<223> OTHER INFORMATION: Fba-KK-Met6 peptide with inserted cysteines at
      positions 5 and 8

<400> SEQUENCE: 23

Tyr Gly Lys Asp Cys Val Lys Cys Asp Leu Phe Asp Tyr Ala Gln Glu
1               5                  10                  15

Lys Lys Pro Arg Ile Gly Gly Gln Arg Glu Leu Lys Lys Ile Thr Glu
            20                  25                  30

<210> SEQ ID NO 24
<211> LENGTH: 32
<212> TYPE: PRT
<213> ORGANISM: Artificial sequence
<220> FEATURE:
<223> OTHER INFORMATION: Fba-KK-Met6 peptide with inserted cysteines at
      positions 5 and 25

<400> SEQUENCE: 24
```

-continued

```
Tyr Gly Lys Asp Cys Val Lys Asp Leu Phe Asp Tyr Ala Gln Glu Lys
1               5                   10                  15

Lys Pro Arg Ile Gly Gly Gln Arg Cys Glu Leu Lys Lys Ile Thr Glu
            20                  25                  30

<210> SEQ ID NO 25
<211> LENGTH: 32
<212> TYPE: PRT
<213> ORGANISM: Artificial sequence
<220> FEATURE:
<223> OTHER INFORMATION: Fba-KK-Met6 peptide with inserted cysteines at
      positions 24 and 27

<400> SEQUENCE: 25

Tyr Gly Lys Asp Val Lys Asp Leu Phe Asp Tyr Ala Gln Glu Lys Lys
1               5                   10                  15

Pro Arg Ile Gly Gly Gln Arg Cys Glu Leu Cys Lys Lys Ile Thr Glu
            20                  25                  30

<210> SEQ ID NO 26
<211> LENGTH: 30
<212> TYPE: PRT
<213> ORGANISM: Artificial sequence
<220> FEATURE:
<223> OTHER INFORMATION: Fba-KK-Met6-toxoid peptide
<220> FEATURE:
<221> NAME/KEY: misc_feature
<222> LOCATION: (30)..(30)
<223> OTHER INFORMATION: Xaa at position 30 is Glu bound to a toxoid,
<220> FEATURE:
<223> OTHER INFORMATION: such as tetanus toxoid or diphtheria toxoid
<220> FEATURE:
<223> OTHER INFORMATION: Predicted synthetic sequence.

<400> SEQUENCE: 26

Tyr Gly Lys Asp Val Lys Asp Leu Phe Asp Tyr Ala Gln Glu Lys Lys
1               5                   10                  15

Pro Arg Ile Gly Gly Gln Arg Glu Leu Lys Lys Ile Thr Xaa
            20                  25                  30
```

CHIMERIC VACCINE AGAINST FUNGAL INFECTIONS

PRIORITY CLAIM

This is the United States national stage of international application PCT/US2015/036593, international filing date Jun. 19, 2015, which claims the benefit of the Jun. 25, 2014 filing date of U.S. provisional patent application Ser. No. 62/016,693 under 35 U.S.C. § 119(e). The complete disclosure of the priority application is hereby incorporated by reference in its entirety.

STATEMENT REGARDING FEDERALLY SPONSORED RESEARCH OR DEVELOPMENT

This invention was made with government support under grant R03 AI107536 awarded by the National Institutes of Health. The United States Government has certain rights in the invention.

TECHNICAL FIELD

This invention pertains to vaccines for active immunization against fungal infections, for example infections by *Candida albicans*.

BACKGROUND ART

Hematogenous candidiasis in humans is a leading cause of nosocomial bloodstream infection in hospital patients. Despite the availability of various antifungal therapies, crude mortality has remained high, ranging from 36 to 90%. There is currently no antifungal vaccine approved for use in humans.

*Candida albicans*, the most common fungal pathogen of humans, has evolved several mechanisms to survive in the host. The complexity of *C. albicans*' antigens and of its host-invasion mechanisms has made it difficult to develop an effective vaccine. There have been some attempts to make multivalent vaccines from mixtures of two or more antigens.

Cell wall peptides have been used as carriers for the small glycan β-1,2-mannotriose. Although initially promising results have been seen, the synthesis of the glycopeptide is difficult and expensive. Other drawbacks of carbohydrate-based vaccines include difficulties in glycan synthesis, difficulties in glycan analysis and purification, and the low affinity of anti-carbohydrate antibodies as compared to that of anti-peptide or anti-protein antibodies. Unlike proteins and nucleic acids, there is no general synthetic route for carbohydrates.

There is an unfilled need for effective, economical vaccines against *Candida*.

REFERENCES

Xin, H., S. Dziadek, D. R. Bundle, and J. E. Cutler. 2008. Synthetic glycopeptide vaccines combining β-mannan and peptide epitopes induce protection against candidiasis. *Proc. Natl. Acad. Sci. USA* 105: 13526-13531.

Xin, H., and J. E. Cutler. 2011. Vaccine and monoclonal antibody that enhance mouse resistance to candidiasis. *Clin. Vaccine Immunol.* 18: 1656-1667.

Xin, H. 2014. Double Chimeric Peptide Vaccine and Monoclonal Antibodies That Protect Against Disseminated Candidiasis. *J Vaccines Vaccine* 5:4.

Xin, H., J. Cartmell, J. J. Bailey, S. Dziadek, D. R. Bundle, and J. E. Cutler. 2012. Self-adjuvanting glycopeptide conjugate vaccine against disseminated candidiasis. *PLoS One* 7.

Cutler, J. E. et al., WO 2012/145666

SUMMARY OF THE INVENTION

I have discovered chimeric peptide vaccines useful for inducing active immunity against *Candida* fungal infections. The chimeric peptide comprises an Fba peptide and an Met6 peptide covalently linked to one another, preferably with a short oligopeptide linker. The two 14-mer peptides Fba and Met6 are derived from two different cell wall proteins of *Candida albicans*: fructose-bisphosphate aldolase (Fba), and methyltetrahydropteroyltriglutamate (Met6). The chimeric double peptide vaccine induces stronger protective immunity against fungal infection than does the Fba peptide alone, the Met6 peptide alone, or a mixture (not covalently linked) of the Fba peptide and the Met6 peptide. Antibodies raised against the chimeric peptides can be used to impart passive immunity against fungal infections. Protective efficacy has been demonstrated against *Candida albicans* infection, and protective efficacy is expected against infection by other clinically significant *Candida* spp.

The Fba peptide and the Met6 peptide are covalently bonded to one another, preferably via an intermediate linker. The linker may be any linker known in the art, provided that the linker does not interfere with the immunogenicity of either the Fba peptide or the Met6 peptide. The linker is preferably a short amino acid linker (e.g., one containing 1, 2, 3, 4, 5, 6, 7, 8, 9, or 10 amino acid residues) such as a double lysine linker (-KK-). Other amino acid linkers include, for example -GGSSGG- [e.g., amino acid residues 15-20 of SEQ ID NO: 5], -GG- and -PP-. The linker may attach to either the C-terminus or the N-terminus of the Fba and Met6 peptides. The peptides may be conjugated to the linker in any orientation. For example a double lysine linker may bond to the Met6 C-terminus and the Fba N-terminus; or to the Met6 N-terminus and the Fba C-terminus. The individual peptides, or the chimeric fusion peptide may be synthesized through means known in the art, including for example synthesis by a peptide synthesizer, or expression in a transgenic host such as *E. coli* or *Saccharomyces cerevisiae*.

The sequence of the Fba peptide is YGKD-VKDLFDYAQE (SEQ ID NO: 1). The sequence of the Met6 peptide is PRIGGQRELKKITE (SEQ ID NO: 2) In a preferred embodiment, the chimeric peptide vaccine is Fba-double lysine linker-Met6, amino acid sequence YGKD-VKDLFDYAQEKKPRIGGQRELKKITE (SEQ ID NO: 3).

The Fba peptide, the Met6 peptide, or both may be modified. For example, any of the amino acids in the peptides may be methylated, which may help enhance biological half-life. Two cysteine residues may be inserted into the Fba domain of the conjugate, the Met6 domain of the conjugate, or both to promote cross-linking and stability. Included within the scope of this invention is any peptide that is the same as SEQ ID NO:3, except that one or more amino acid residues are methylated, or that two cysteine residues have been inserted, or both. The linker may be any moiety (peptide or otherwise) that does not substantially interfere with immunogenicity. In a preferred embodiment, the linker is an oligopeptide that is readily cleaved by enzymes present in the cell, such as a double lysine K-K linker. Many such linkers are known in the art. Non-limiting examples of unmodified and modified peptides within the scope of the invention are shown in Table 1. In Table 1, an underlined letter indicates a methylated amino acid.

TABLE 1

Examples of Modified and Unmodified Chimeric Peptides useful as vaccines against *Candida* and other fungal pathogens

| Sequence | SEQ ID NO | Comments |
| --- | --- | --- |
| YGKDVKDLFDYAQE | SEQ ID NO: 1 | Fba |
| PRIGGQRELKKITE | SEQ ID NO: 2 | Met6 |
| YGKDVKDLFDYAQEKKPRIGGQRELKKITE | SEQ ID NO: 3 | Fba-KK-Met6 |
| PRIGGQRELKKITEKKYGKDVKDLFDYAQE | SEQ ID NO: 4 | Met6-KK-Fba |
| YGKDVKDLFDYAQEGGSSGGPRIGGQRELKKITE | SEQ ID NO: 5 | Fba-GGSSGG-Met6 |
| PRIGGQRELKKITEGGYGKDVKDLFDYAQE | SEQ ID NO: 6 | Met6-GG-Fba |
| YGKDVKDLFDYAQEPPPRIGGQRELKKITE | SEQ ID NO: 7 | Fba-PP-Met6 |
| YGKDVKDLFDYAQEKKPRIGGQRELKKITE | SEQ ID NO: 8 | Fba-KK-Met6 methylated at position 1 |
| YGKDVKDLFDYAQEKKPRIGGQRELKKITE | SEQ ID NO: 9 | Fba-KK-Met6 methylated at position 2 |
| YGKDVKDLFDYAQEKKPRIGGQRELKKITE | SEQ ID NO: 10 | Fba-KK-Met6 methylated at position 3 |
| YGKDVKDLFDYAQEKKPRIGGQRELKKITE | SEQ ID NO: 11 | Fba-KK-Met6 methylated at position 5 |
| YGKDVKDLFDYAQEKKPRIGGQRELKKITE | SEQ ID NO: 12 | Fba-KK-Met6 methylated at position 6 |
| YGKDVKDLFDYAQEKKPRIGGQRELKKITE | SEQ ID NO: 13 | Fba-KK-Met6 methylated at position 8 |
| YGKDVKDLFDYAQEKKPRIGGQRELKKITE | SEQ ID NO: 14 | Fba-KK-Met6 methylated at position 9 |
| YGKDVKDLFDYAQEKKPRIGGQRELKKITE | SEQ ID NO: 15 | Fba-KK-Met6 methylated at position 11 |
| YGKDVKDLFDYAQEKKPRIGGQRELKKITE | SEQ ID NO: 16 | Fba-KK-Met6 methylated at position 20 |
| YGKDVKDLFDYAQEKKPRIGGQRELKKITE | SEQ ID NO: 17 | Fba-KK-Met6 methylated at position 25 |
| YGKDVKDLFDYAQEKKPRIGGQRELKKITE | SEQ ID NO: 18 | Fba-KK-Met6 methylated at position26 |
| YGKDVKDLFDYAQEKKPRIGGQRELKKITE | SEQ ID NO: 19 | Fba-KK-Met6 methylated at position 27 |
| YGKDVKDLFDYAQEKKPRIGGQRELKKITE | SEQ ID NO: 20 | Fba-KK-Met6 methylated at positions 1 and 8 |
| YGKDVKDLFDYAQEKKPRIGGQRELKKITE | SEQ ID NO: 21 | Fba-KK-Met6 methylated at positions 5 and 8 |

TABLE 1 -continued

Examples of Modified and Unmodified Chimeric Peptides useful as vaccines against *Candida* and other fungal pathogens

| Sequence | SEQ ID NO | Comments |
|---|---|---|
| YGKDVKDLFDYAQEKKPRIGGQRELKKITE | SEQ ID NO: 22 | Fba-KK-Met6 methylated at positions 5 and 25 |
| YGKDCVKCDLFDYAQEKKPRIGGQRELKKITE | SEQ ID NO: 23 | Fba-KK-Met6 with inserted cysteines at positions 5 and 8 |
| YGKDCVKDLFDYAQEKKPRIGGQRCELKKITE | SEQ ID NO: 24 | Fba-KK-Met6 with inserted cysteines at positions 5 and 25 |
| YGKDVKDLFDYAQEKKPRIGGQRCELCKKITE | SEQ ID NO: 25 | Fba-KK-Met6 with inserted cysteines at positions 24 and 27 |
| YGKDVKDLFDYAQEKKPRIGGQRELKKITEX | SEQ ID NO: 26 | Fba-KK-Met6-toxoid; X designates a carrier, such as tetanus toxoid or diphtheria toxoid |

MODES FOR CARRYING OUT THE INVENTION

Figure 1A:
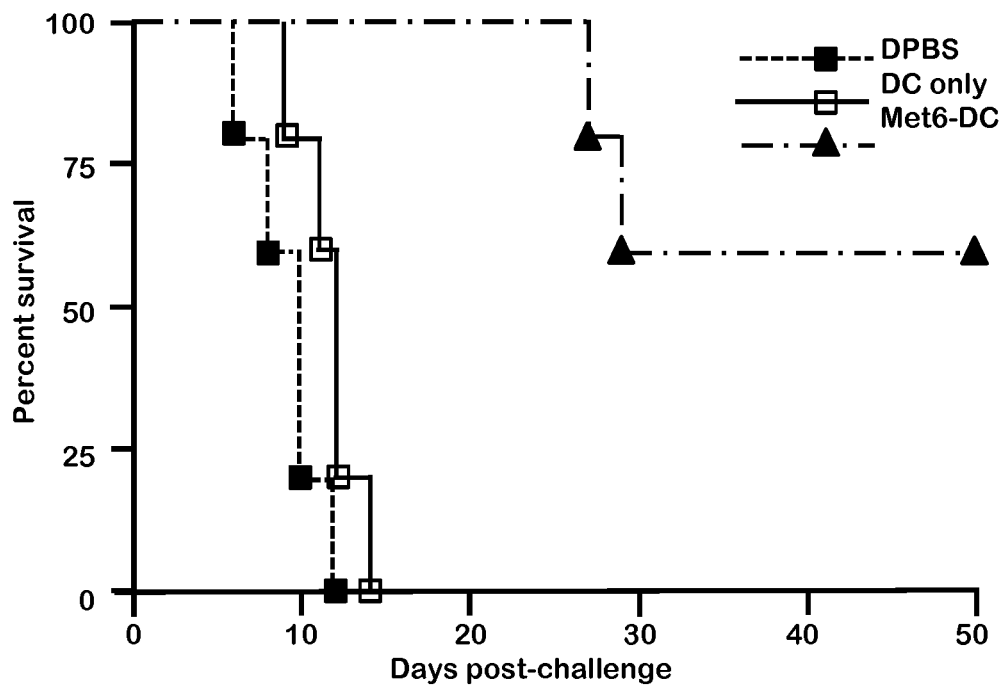
FIG. 1A depicts survival rate as a function of time following a lethal dose of *C. albicans* (strain SC5314) for different groups of mice given peptide vaccine or control.

Optionally, the chimeric peptide vaccine may be further covalently bonded to additional components. The additional components may be linked to the N-terminus, the C-terminus, the linker, or an amino acid in the Fba or Met6 domain, and in any orientation. Such components may, for example, enhance the utility of the chimeric peptide vaccine for human use. Such optional components may include, for example, a Multiple Antigen Peptide (MAP) system such as 4 MAP and 8 MAP; or a protein carrier or adjuvant, such as tetanus toxoid or diphtheria toxoid.

The chimeric peptides are used as vaccines to impart active immunity against fungal infections. The vaccine is administered to a mammal in need thereof, for example a human being. The vaccine may also provide immunity against *Candida* species of medical significance, including not only *C. albicans*, but also such species as *C. glabrata, C. tropicalis, C. gulliermodii,* and *C. lusitaniae*.

Embodiments of the present invention include hybrid cell lines (hybridomas), monoclonal antibodies, and methods utilizing the monoclonal antibodies, where the monoclonal antibodies bind an antigen of *Candida*, for example monoclonal antibodies that selectively bind Met6. In certain embodiments, hybrid cell line designated M2-4 is provided which produces a monoclonal antibody that selectively binds Met6; the monoclonal antibody itself is also designated M2-4. The M2-4 and E2-9 hybridoma cell lines are stored at the Louisiana State University Health Sciences Center, New Orleans, La.; and samples of those hybridoma lines will be provided to technically qualified individuals throughout the enforceable life of this patent, upon request to the Office of Technology Management, Louisiana State University Health Sciences Center, New Orleans, La. In certain embodiments, an effective amount of the monoclonal antibodies of the present invention, such as monoclonal antibody M2-4, may be administered to a mammal in need thereof to protect against fungal infections. In certain embodiments, the fungal infection is *Candida albicans*. In still other embodiments, the monoclonal antibodies may protect against other infection by other *Candida* species.

Embodiments of the present invention include therapeutic compositions containing one or more protective antibodies, and methods of using those therapeutic compositions to provide passive immunity. In certain embodiments, the therapeutic composition comprises antibodies that bind *Candida* cell surface antigens, such as antibodies against Fba and Met6. For example, the therapeutic composition may comprise MAb M2-4 (against Met6) and MAb E2-9 (against Fba).

The therapeutic compositions may be particularly well-suited for treating immunosuppressed individuals, whose bodies are otherwise unable to produce antibodies of their own against fungal antigens. The therapeutic compositions may also comprise a pharmaceutically acceptable carrier.

The chimeric double peptide vaccine may be administered to a mammal by any means known in the art for vaccine delivery. Because peptides are usually degraded rapidly once injected into the body, in a preferred embodiment the double peptide chimera is bound to a carrier molecule such as tetanus toxoid (TT) or diphtheria toxoid (DT).

Typical compositions also comprise a pharmaceutically acceptable carrier. The active immunogenic ingredient may be mixed with an excipient that is pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances that enhance the effectiveness of the vaccine such as wetting or emulsifying agents, pH-buffering agents, adjuvants or immunopotentiators. Optionally, an adjuvant may be administered with the chimeric peptide, for example alum, tetanus toxoid, or diphtheria toxoid.

The term "immunologically effective amount" refers to an amount of vaccine that induces protective immunity in the recipient, whether administered in one dose or in multiple doses at different times in a vaccination series, including a prime/boost administration series, and also including a booster dose delivered some time following an initial immunization.

The vaccine may be administered by any means known in the art. For a peptide vaccine it is usually preferred to administer by injection, whether intramuscular, subcutaneous, intraperitoneal, or intravenous.

The term "therapeutically effective amount" refers to the quantity of a substance required to be therapeutically effective to prevent or treat the symptoms of a fungal infection.

The term "active immunization" refers to the induction of an active immune response by a mammal. The term "passive immunization" refers to the transfer of antibodies or immune serum to a mammal to provide temporary benefit.

The term "immune response" refers to the reaction of the body to foreign substances (antigens), such as disease producing microorganisms. The response includes the production of antibodies and the development of cell-mediated immune response.

The term "adjuvant" refers to a non-antigenic substance (such as aluminum hydroxide, monophosphoryl lipid A, tetanus toxoid, or diphtheria toxoid) that, in combination with an antigen, enhances antibody production by inducing an inflammatory response, which leads to a local influx of antibody-forming cells. Adjuvants are used therapeutically in the preparation of vaccines, as they can increase the production of antibodies against small quantities of antigen and lengthen the period of antibody production. Adjuvants may increase immunoprotective antibody titers, or cell mediated immunity response, or both.

The term "vaccine" refers to a composition or compound (an antigen, or a composition including an antigen) used to stimulate an immune response in a mammal and so to confer resistance to disease or infection in that mammal, including the ability of the immune system to remember the previously encountered antigen.

EXAMPLES

The following examples are further illustrative of the present invention. These examples are not intended to limit the scope of the present invention and provide further understanding of the invention.

Summary of Results

We combined the Fba and Met6 peptides into a chimeric "double peptide" vaccine against *C. albicans*, resulting in a more effective vaccine. Following the immunization protocol as otherwise generally described in Xin, H., S. Dziadek, D. R. Bundle, and J. E. Cutler. 2008 (Synthetic glycopeptide vaccines combining β-mannan and peptide epitopes induce protection against candidiasis. *Proc. Natl. Acad. Sci. USA* 105: 13526-13531), we tested and compared the efficacy of the chimeric double peptide vaccine with the efficacy of the single peptide vaccines (Fba or Met6) individually, as well as a vaccine containing a mixture of the two individual peptides (i.e., not fused into a chimeric double peptide). The chimeric double peptide vaccine (Fba-Met6 conjugate) provided significantly and substantially enhanced protective immunity as compared to the other vaccines, evidenced by a 100% survival rate and much lower CFUs in kidneys. Our work demonstrated that the double epitope vaccine provides superior immunity against *C. albicans* Infections.

We also evaluated the protective effect of two monoclonal antibodies, E2-9 and M2-4, given alone, or in a double-MAb combination (E2-9+M2-4) to naïve mice. While the use of individual MAb (E2-9 or M2-4) gave promising results, the combination of MAb E2-9 and MAb M2-4 gave the best passive transfer protection.

Example 1. Materials and Animals

*Candida* Strains and Culture Conditions.

*C. albicans* strains 3153A and SC5314 (available through American Type Culture Collection) were grown to stationary phase in glucose-yeast extract-peptone broth at 37° C., washed and suspended to a cell concentration of $5\times10^6$/ml in Dulbecco's PBS (DPBS; Sigma). These suspensions were then used to infect mice intravenously (i.v.). *C. albicans* strain 3153A was also used for serum antibody absorption assays, immunofluorescence staining, and flow cytometry.

Mice.

BALB/c or C57BL/6 female mice (National Cancer Institute Animal Production Program, Frederick Md.) 5 to 7 weeks old were used throughout. Mice were maintained in our AAALAC-certified animal facility. All animal experiments were conducted in accordance with protocols approved by the Institutional Animal Care and Use committee (IACUC) at Children's Hospital Research Institute in New Orleans.

Example 2. Isolation and Culture of Dendritic Cells (DCs) from Mouse Bone Marrow Dendritic cells (DCs) were generated from mouse bone marrow. Briefly, donor mice were euthanized by $CO_2$ asphyxiation, their long bones and tibias were aseptically removed, bone marrow was flushed from the bones by forcibly injecting several ml of RPMI-1640, and clumps were removed or dispersed by gentle pipetting through a sterile 70 mm cell strainer. Red blood cells were lysed (ACK lysing buffer, 0.15 M $NH_4Cl$, 1.0 mM $KHCO_3$, 0.1 mM EDTA) for 4 min. The bone marrow cells then remaining were suspended in complete medium [CM, RPMI-1640 supplemented with 10% FBS (FBS), 2 mM L-glutamine, 1% nonessential amino acids, 100 units/ml penicillin, and 100 µg/ml streptomycin], adjusted to $2 \times 10^5$ cells per ml, plated in 6-well plates at 5 ml per well, and cultured for up to 9 days in the presence of 40 ng/ml of rmGM-CSF and rmIL-4 (R&D Systems) at 37° C., 5% $CO_2$. On days 4 and 7 of culture, the same amount of fresh GM-CSF and IL-4 was again added to the wells.

Examples 3-7. Peptide Vaccines, Peptide-8MAP Vaccines, and Chimeric Double Peptide Vaccine Fba peptide and Met6 peptide were separately conjugated to a multiple antigenic peptide (MAP). MAP is a vehicle for producing high-titer anti-peptide antibodies and synthetic peptide vaccines. This system uses the α- and ε-amino functional groups of lysine to form a core to which multiple peptides can be attached. The MAP lysine core displayed approximately eight copies of each peptide epitope, to form Fba-8Map and Met6-8MAP. Fba peptide, Met6 peptide, Fba-8MAP conjugate, Met6-8MAP conjugate, and Fba-KK-Met6 chimeric double peptide (SEQ ID. NO: 3) were synthesized commercially by GenScript (Piscataway, N.J.).

Example 8. Peptide-Pulsed Immunization of Dendritic Cells

Different groups of dendritic cells (DCs) were pulsed in vitro with Fba peptide, Met6 peptide, Fba-Met6 chimeric double peptide, or a mixture of the two peptides Fba and Met6. Briefly, DCs in culture were pulsed with the peptide antigen (1 µM) on day 6. On day 7, $PGE_2$ ($10^{-7}$ M) was added along with LPS (2 µg/ml, Sigma) for 24 h. On day 9, antigen-pulsed DCs were washed extensively and $5 \times 10^5$ cells in 200 µl DPBS were injected into mice i.p. with complete Freund's adjuvant as the priming dose. The mice were boosted i.p. at day 14 with fresh antigen-pulsed DCs and adjuvant. The mice were again boosted i.p. at day 28 with fresh antigen-pulsed DCs, but the final boost used no adjuvant.

Example 9. Immunizations with Peptide Vaccines Using the Human-Approved Adjuvant Alum Fba-8MAP and Met6-8MAP peptides were administered as a mixture using alum (aluminum hydroxide gel, Sigma) as adjuvant. Mice were immunized by s.c. injection with 100 µl of 2.5 µg of either Fba-8MAP conjugate or Met6-8MAP conjugate with 50 µg alum on days 1, 21 and 42. Sera from groups of mice given DPBS buffer only, or adjuvant only were used as negative controls.

Example 10. Serological Assays

Sera antibody titers were analyzed by ELISA. For DC-based immunization, the control groups were mice given DCs alone, or given DPBS alone, for all three injections. For the Fba-8MAP or Met6-8MAP peptide administered with alum, the control groups were mice given adjuvant alone or DPBS buffer. Fbb-8MAP or Met6-8MAP was dissolved at 5 µg/ml in PBS (pH 7.4), and used to coat 96-well ELISA plates with duplicate, serial, 2-fold dilutions of samples of each immune serum and control serum. Each well was treated with secondary antibody (goat anti-mouse polyvalent Ig-HRP, Sigma) and substrate (o-phenylenediamine and $H_2O_2$). Optical density was measured at 492 nm.

Example 11. Monoclonal Antibodies (MAbs)

Hybridoma clones were generated from mice vaccinated with Fba-DCs or Met6-DCs, to produce the Fba peptide-specific IgM monoclonal antibody E2-9, or the Met6 peptide-specific IgG3 monoclonal antibody MAb M2-4. Briefly, BALB/c mice were immunized by injecting the synthetic-peptide-pulsed-DCs to stimulate production of antibodies against the respective peptide, as otherwise described above. Ten days after the second booster, serum was taken from each animal to identify those animals with the highest anti-peptide titers. The mice with the highest titers were sacrificed, their spleens were removed, and single-cell suspensions were prepared by standard means. Hybridoma clones were established by standard means, using polyethylene glycol to facilitate fusion of spleen cells to an SP2/0-AG14 myeloma cell line. Hybridoma clones were screened by ELISA for production of specific anti-peptide antibody; only the highest titers and most rapidly growing clones were selected for subsequent cloning, 3× or more by limiting dilution.

The hybridoma cell lines were initially grown in antibiotic-free RPMI 1640 medium (Sigma) supplemented with 10% fetal bovine serum (Invitrogen) and 2 mM L-glutamine (Sigma) at 37° C. under 5% $CO_2$ For antibody production, the hybridoma clones were grown in antibiotic-free, BD cell MAb serum-free medium (supplemented with 1.1 mg bovine serum albumin/ml) in a CELLine device (BD, Bedford, Mass.). The supernatant was collected, and MAb was purified by affinity chromatography on a Protein A Sepharose 4FF column (GE Healthcare, USA). The isotype of MAb was determined with a Mouse Monoclonal Antibody Isotyping Kit (Pierce, USA).

Example 12. Fungal Challenge and Assessment of Protection

Two weeks after the second boost, immunized and control mice were both infected i.v. with a lethal dose of live *C. albicans* yeast cells ($5 \times 10^5$ in 0.1 ml of DPBS), prepared as described above. Passively immunized mice (see below) also received the same challenge dose. Protection was evaluated by monitoring animal survival for 50-60 days. The mice were monitored for the development of a moribund state: defined as being listless, disinterested in food or water, and nonreactive to finger probing. Once a mouse was deemed moribund, it was sacrificed and its kidneys were homogenized in DPBS and plated onto a nutrient agar to determine the number of colony forming units of yeast (CFUs).

Example 13. Passive Transfer of MAbs Intraperitoneally (i.p.)

The protective effect of the monoclonal antibodies M2-4 and E2-9 was examined in passive transfer experiments. The MAb E2-9 was diluted in DPBS (0.2 µg/µl), to give a 100,000 ELISA titer against Fba-MAP peptide coated on a plate. The MAb M2-4 was diluted in DPBS (0.5 µg/µl) to give a 100,000 ELISA titer against Met6-MAP peptide coated on a plate. Mice received intraperitoneally 0.5 ml of MAb M2-4, or 0.5 ml of MAb E2-9, or 1.0 ml of the two MAbs combined (0.5 ml of each). Negative control mice were injected intraperitoneally with 0.5 ml of vehicle containing MAbs that had been absorbed with *C. albicans* yeast cells (3153A), or with 0.5 ml of vehicle (DPBS). For each treatment, 6- to 8-week-old female BALB/c mice (NCI) were injected intraperitoneally with 0.5 ml of test MAb, 1.0 ml of a mixture of the two MAbs, or negative control materials, followed 4 h later by a 0.1 ml intravenous suspension containing $5 \times 10^6$ yeast cells per milliliter in DPBS. Mice were divided into groups containing five mice each, and the experiments were carried out in triplicate. In some experiments, mice were given the same dose of antibodies (MAb E2-9 or MAb M2-4) or control materials every other day for two weeks. All mice were sacrificed on day 50.

Statistical Analysis.

Survival times were evaluated statistically by Kaplan-Meier estimator (GraphPad Prism, version 4). All analyses included five mice per group (n=5). A two-tailed t test was used.

Results

Figure 1B:
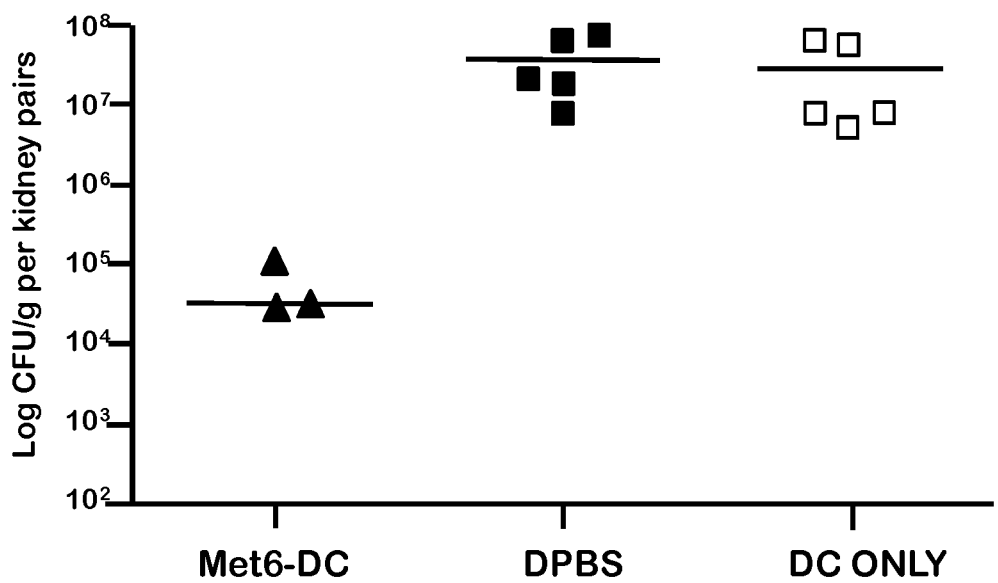
FIG. 1B depicts (on a logarithmic scale) the observed CFUs levels in the kidneys for the different groups of mice.
Figure 1C:
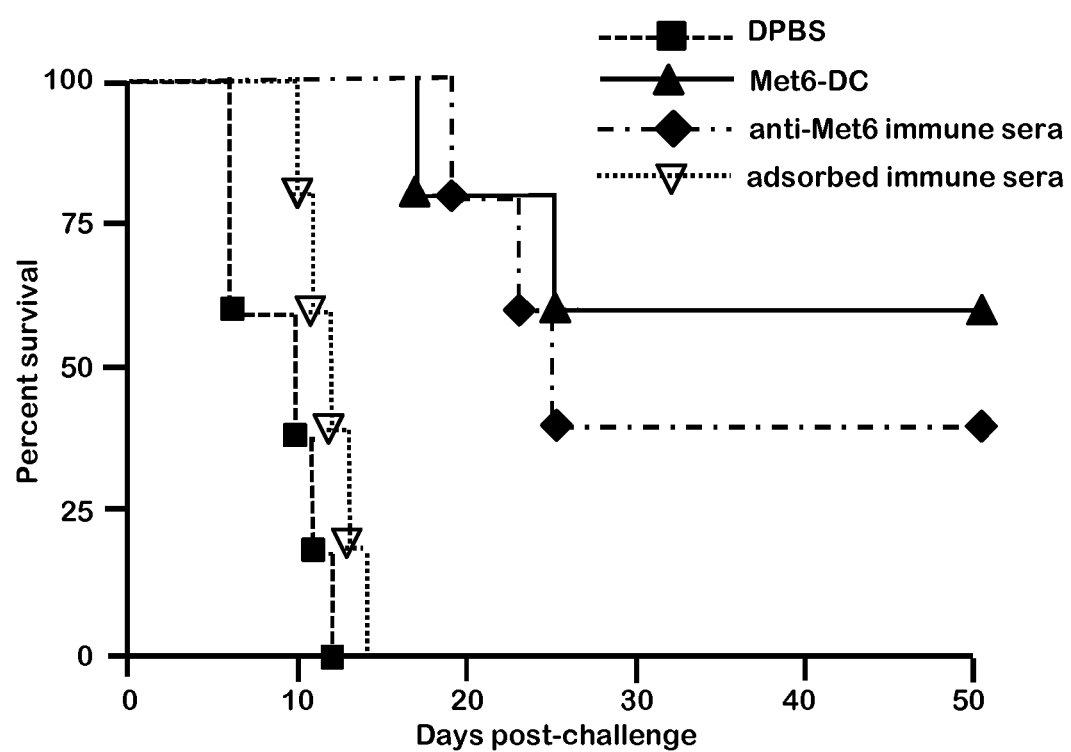
FIG. 1C depicts survival rate as a function of time following a lethal dose of *C. albicans* (strain SC5314) for the different groups of mice given immune globulin or control.

Example 14. Vaccination with Met6 Peptide Induced Antibody Production and Provided Protective Immunity Against Disseminated Candidiasis in Mice Peptide Fba-pulsed immunization of DCs induced robust protective responses, mediated by Fba peptide-specific antibodies (data not shown). Likewise, peptide Met6-pulsed immunization of DCs also induced robust protective responses, mediated by Met6 peptide-specific antibodies. FIG. 1A depicts survival following Met6 pulsed immunization and subsequent *Candida* challenge in mice. FIG. 1B depicts a reduced or non-detectable fungal burden (colony forming units, CFUs) in kidneys from these mice. The kidneys are target organs in disseminated candidiasis. Met6-specific antibodies appeared to be responsible for the anti-*Candida* protection, as demonstrated by experiments in which passive transfer of whole immune serum from Met6 peptide-vaccinated mice conferred protection to naïve mice (FIG. 1C). Such protection was not conferred by control DPBS buffer, nor by immune serum pre-absorbed by fungal cells prior to the passive transfer.

Vaccination with Met6 peptide by the dendritic cell approach induced significant protection against experimental disseminated candidiasis in mice. FIG. 1A depicts survival rates as a function of time for different groups of mice given peptide vaccine or control following a lethal dose of *C. albicans* (strain SC5314). Vaccination with Met6 peptide significantly prolonged survival time as compared to that for control mice (P<0.01).

FIG. 1B depicts (on a logarithmic scale) the observed CFUs levels in the kidneys for the different groups of mice. The immunized mice had greatly reduced or even non-detectable CFUs in their kidneys (P<0.001) as compared to levels seen for the control mice. (Note: As used here, "non-detectable" means, using the classic method employed to determine colony-forming units (CFU) in the pair of kidneys from each mouse, not even a single colony could be grown from 100 µl of kidney homogenate, a measured value of 0. Because kidney homogenate was serially diluted to a dilution factor of 50, "non-detectable" means either that zero CFUs were actually present in the total kidney homogenate, or if any were present the total number of CFUs in the total kidney homogenate was below a number on the order of approximately 50. Mice displaying titers below the detection limit were assigned an arbitrary value of 50 CFU, and were labeled "ND" (non-detectable).)

Antibody was responsible for protection against disseminated candidiasis. FIG. 1C depicts survival rate as a function of time following a lethal dose of *C. albicans* (strain SC5314) for the different groups of mice given immune globulin or control. Serum from mice immunized with the Met6 peptide imparted significantly enhanced protection against disseminated *C. albicans* infection as compared to animals receiving control materials. Note that the survival rates of the positive control mice were similar to the survival rates of the naïve mice that received immune serum. (Compare FIGS. 1A and 1C.). Also note that absorption with *C. albicans* before the passive transfer removed the protective value of the immune serum.

Example 15. Vaccination with a Mixture of the Two Peptides Did not Substantially Alter Antibody Production in Mice, and Did not Substantially Alter Protection Against Disseminated Candidiasis, as Compared to Vaccination with Either of the Single Peptides Alone We attempted to induce greater protection by immunizing mice with a mixture of the two peptides Fba and Met6. Using the dendritic cell (DC) approach, we compared the vaccine efficacy of the Met6 peptide, the Fba peptide, and a mixture of the two peptides. Immunized groups that received the peptide Fba vaccine, the peptide Met6 vaccine, or a vaccine containing a mixture of the Fba and Met6 peptides all showed 60-80% survival 50 days post-challenge. All three peptide-vaccinated groups survived significantly longer following lethal challenge as compared to control groups receiving DPBS only or DC only. See FIG. 2A. Mice immunized with a single peptide or with the two peptide mixture showed greatly reduced or even non-detectable fungal CFUs in kidneys as compared to control animals (p<0.0001). See FIG. 2B. We were disappointed, however, to find that a mixture of the two peptides did not meaningfully increase protection as compared to vaccination with either individual peptide. (Compare FIG. 1A). The mice vaccinated with the two peptide mixture did not show significantly lower CFUs in kidneys as compared to the individual peptide groups. See FIG. 2B. There was no significant difference in peptide-related antibody responses between the Fba/Met6 mixture group and that for the mice receiving individual peptides (data not shown).

Figure 2A:
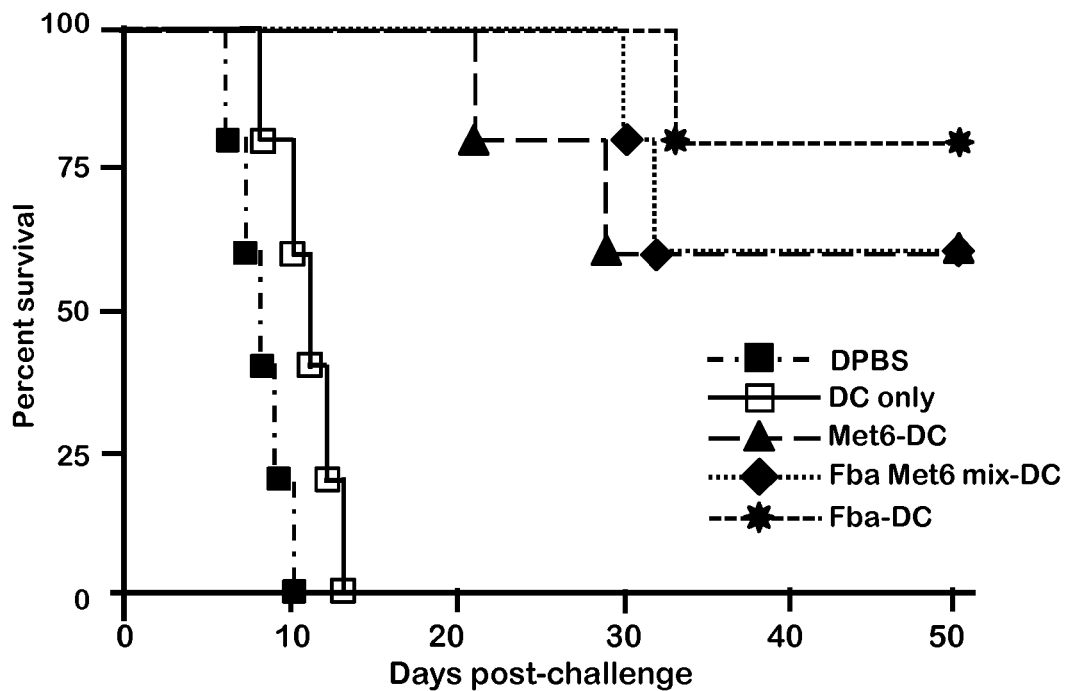
FIG. 2A depicts survival rate as a function of time following a lethal dose of *C. albicans* (strain SC5314) for different groups of mice vaccinated with the peptide Fba, vaccinated with the peptide Met6, vaccinated with a mixture of the Fba and Met6 peptides, or given control.

FIG. 2A depicts survival rate as a function of time following a lethal dose of *C. albicans* (strain SC5314) for different groups of mice vaccinated with the peptide Fba, vaccinated with the peptide Met6, vaccinated with a mixture of the Fba and Met6 peptides, or given control. The mice receiving the peptide vaccines showed 60-80% survival 50 days post-challenge, and all three peptide-vaccinated groups survived significantly longer as compared to DPBS or DC only controls following the lethal challenge. Peptide Fba induced the best protection, but the differences between the survival rates for the three types of peptide vaccination were not significantly different.

Figure 2B:
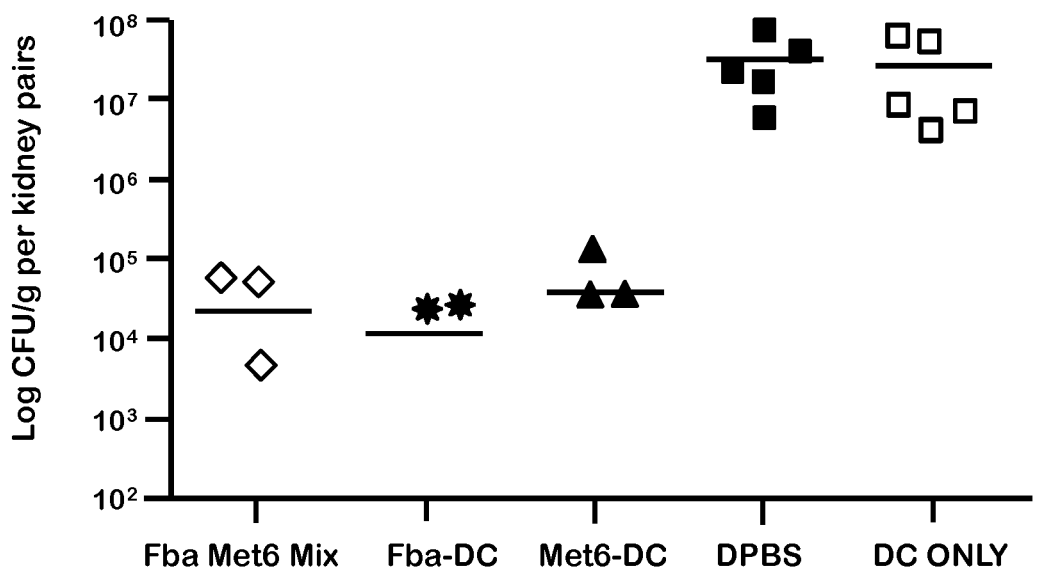
FIG. 2B depicts (on a logarithmic scale) the observed CFUs levels in the kidneys for the different groups of mice.

FIG. 2B depicts (on a logarithmic scale) observed CFU levels in the kidneys for the different groups of mice. Peptide- or peptide mixture-immunized groups had greatly reduced or even non-detectable fungal CFUs in kidneys as compared to control animals ($p<0.0001$). However, there was no significant difference in CFU level among the Fba-only group, the Met6-only group, and the Fba/Met6 mixture group. Likewise, there was no significant difference in peptide-related antibody responses between the groups vaccinated with the individual peptides and the group vaccinated with the two-peptide mixture (data not shown).

Example 16. Peptides Fba-8MAP and Met6-8MAP Administered Along with Alum Induced Only Modest Protection Against Candidiasis The DC-based immunization approach can help overcome otherwise weak immune responses against small molecules. As discussed above, DC-based immunization successfully protected mice against disseminated candidiasis using the small synthetic peptides Fba and Met6 as vaccines. However, DC-based immunization is not ideal for large-scale use in humans, due to the procedure's complexity and expense. To try to overcome this practical impediment, each peptide was separately conjugated to a multiple antigenic peptide (MAP) system for immunization. In the MAP system a lysine-rich core was conjugated to and displayed approximately eight copies of the particular peptide epitope. Results using the MAP system showed only a modest improvement, which was disappointing.

The Fba-8MAP conjugate or the Met6-8MAP conjugate was administered as a mixture with an alum adjuvant (aluminum hydroxide gel, Sigma). Mice were immunized by subcutaneous (s.c.) injection of 0.1 ml of DPBS buffer containing either 2.5 µg of Fba-8MAP or 2.5 µg of Met6-8MAP, mixed with 50 µg alum, on days 1, 21 and 42. Negative control groups of mice were given the same volume of DPBS buffer, or the same volume of DPBS buffer with alum adjuvant. Groups immunized with peptide-pulsed DCs were used as positive controls.

Serum samples were collected 14 days after immunization, diluted 1:200, and tested by ELISA on plates coated with the applicable peptide-8MAP conjugate. After the first booster, immune sera from mice immunized with Fba-8MAP conjugate or Met6 peptide (with alum adjuvant) showed antibody responses only about 4-5 fold greater than that for the negative control mice receiving DPBS or adjuvant only. However, the immune responses to the MAP conjugates were substantially weaker than those induced by peptide-pulsed DC immunization. See FIG. 3A.

Figure 3A:
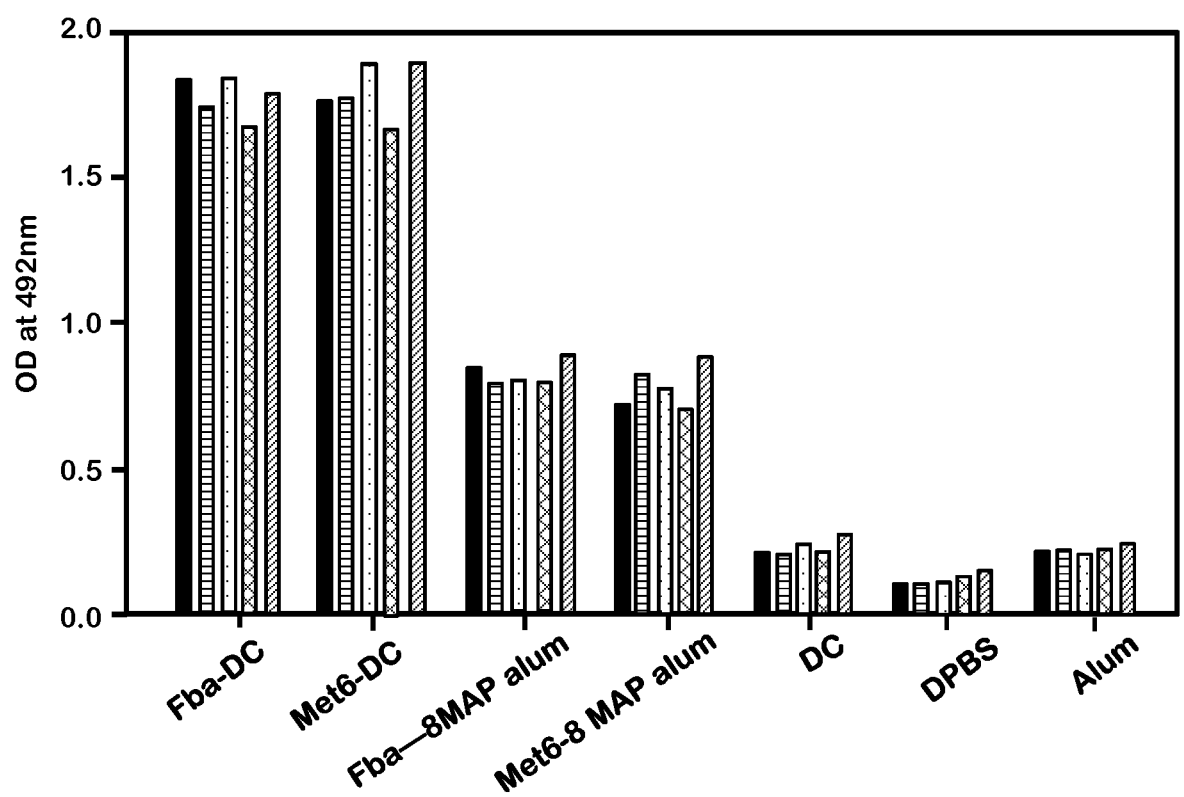
FIG. 3A depicts optical density measurements at 492 nm for adsorbed ELISA samples following the first booster for immune serum from mice immunized with peptide-8MAP in alum, negative controls, and positive controls (peptide-pulsed DC immunization).

FIG. 3A depicts optical density measurements at 492 nm for the adsorbed ELISA samples following the first booster for immune serum from mice immunized with peptide-8MAP in alum, for negative controls, and for positive controls (peptide-pulsed DC immunization).

Following the second booster immunization, an IgM to IgG isotype switch was seen for both the Fba-specific and the Met6-specific antibodies. The isotype switch was seen in both peptide-DC and peptide-8MAP immunized mice (data not shown), and suggests that an immune memory response had been induced.

Following challenge with a lethal dose of live *C. albicans* cells (strain 3153A), the groups vaccinated with Fba-8MAP and alum, or Met6-8MAP and alum had prolonged survival times as compared to the two control groups. However the protection was less effective than that induced with the peptide-pulsed DCs. Mice immunized with Fba-8MAP and alum, or Met6-8MAP and alum had only a 40% survival rate at 50 days, while the groups immunized with peptide-pulsed DCs showed better survival, 60-80%. See FIG. 3B. The immunized groups had reduced levels of kidney CFUs as compared to controls. The Fba peptide-pulsed group and the Met6 peptide-pulsed DC group showed the lowest kidney CFU levels. See FIG. 3C.

Figure 3B:
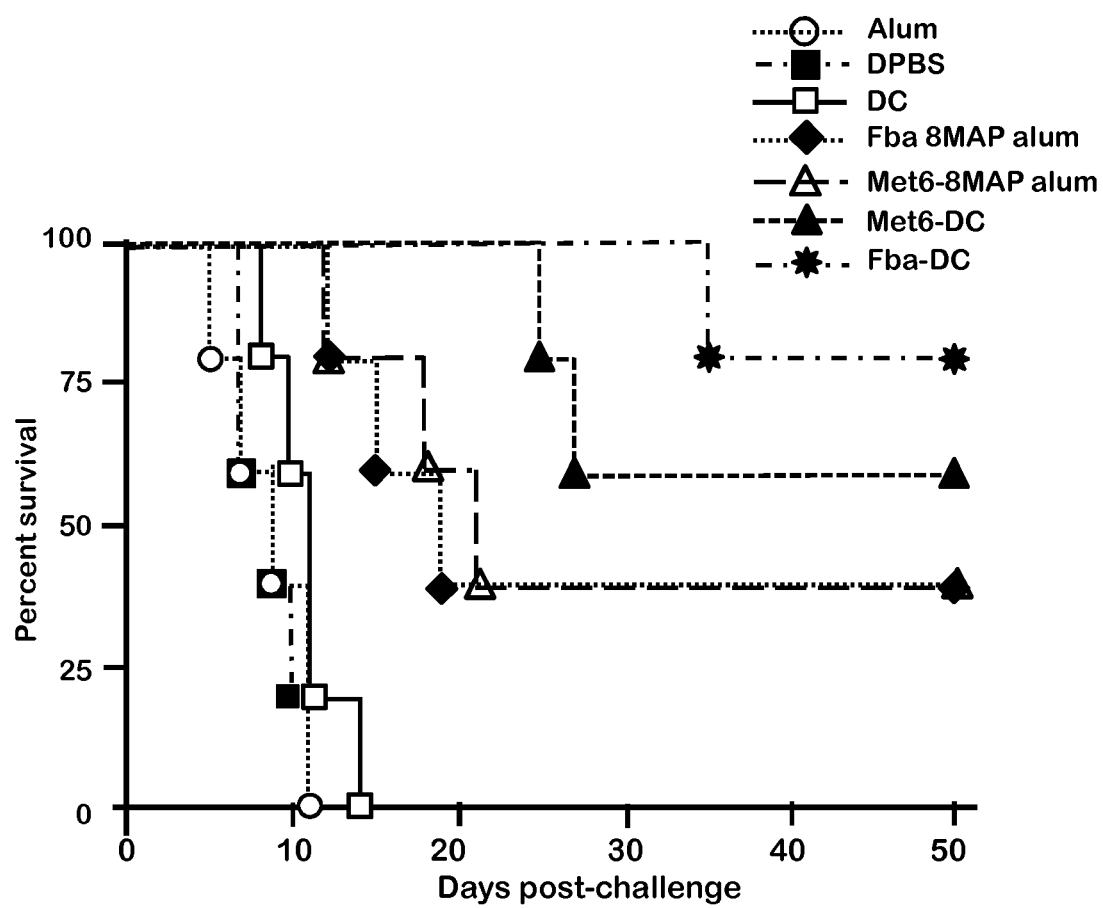
FIG. 3B depicts survival rates as a function of time up to 50 days for the various groups following challenge with a lethal dose of live *C. albicans* cells (3153A).

FIG. 3B depicts survival rates as a function of time up to 50 days for the various groups following challenge with a lethal dose of live *C. albicans* cells (3153A). The groups vaccinated with Fba-8MAP and alum, or Met6-8MAP and alum showed prolonged survival times as compared to the two control groups ($p<0.01$). However the protection was less effective than that induced with peptide-pulsed DCs.

Figure 3C:
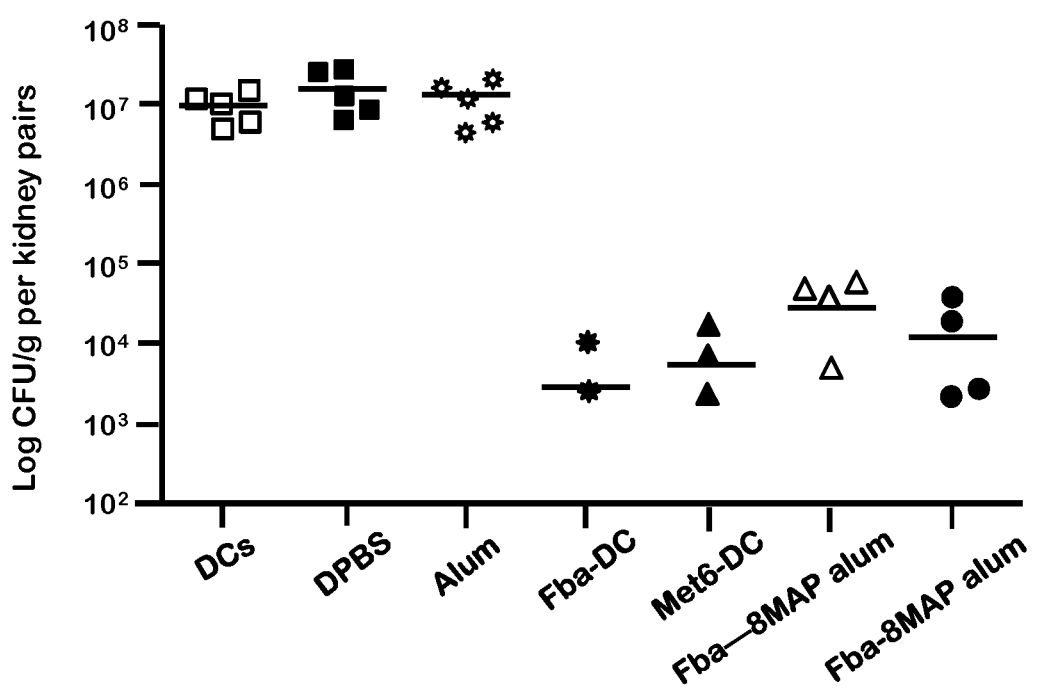
FIG. 3C depicts (on a logarithmic scale) the observed CFUs levels in the kidneys for the different groups of mice. All immunized groups had significantly lower levels of live fungal cells in the kidneys as compared to controls (P<0.001). The Fba and Met6 peptide-pulsed DC groups had the lowest CFU levels in the kidneys.

FIG. 3C depicts (on a logarithmic scale) observed CFUs levels in the kidneys for the different groups of mice. All immunized groups had lower levels of live fungal cells in the kidneys as compared to controls ($P<0.001$). The Fba and Met6 peptide-pulsed DC groups had the lowest CFU levels.

The results obtained by conjugating the peptides to a multiple antigenic peptide (MAP) system were disappointing. Only modest improvements in outcome were seen.

Example 17. Chimeric Double Peptide-Pulsed DC Vaccination Induced Strong Immune Protection Against Disseminated Candidiasis in Mice As described above, neither a mixture of the two peptides, nor conjugating the peptides to a multiple antigenic peptide produced substantially improved results over those seen with single peptide vaccines. Surprisingly, vaccination with a chimeric double peptide linking the Fba and Met6 peptides substantially improved protective immunity.

In one embodiment the C-terminus of Fba peptide was conjugated to the N-terminus of Met6 peptide through a preferred double lysine linker (-KK-). Although other linkers might also be used, double lysine is currently preferred because it is the target sequence of the lysosomal protease cathepsin B, which is used in MHC-II antigen presentation. If another linker is used, it is preferred that the linker also be readily cleaved in vivo, although such cleavage is not required. Neither the linker nor the cleavage products (if any) should interfere with the immunogenicity of the Fba and Met6 peptides.

Mice immunized with Fba-DC or with Met6-DC were used as positive controls.

Figure 4A:
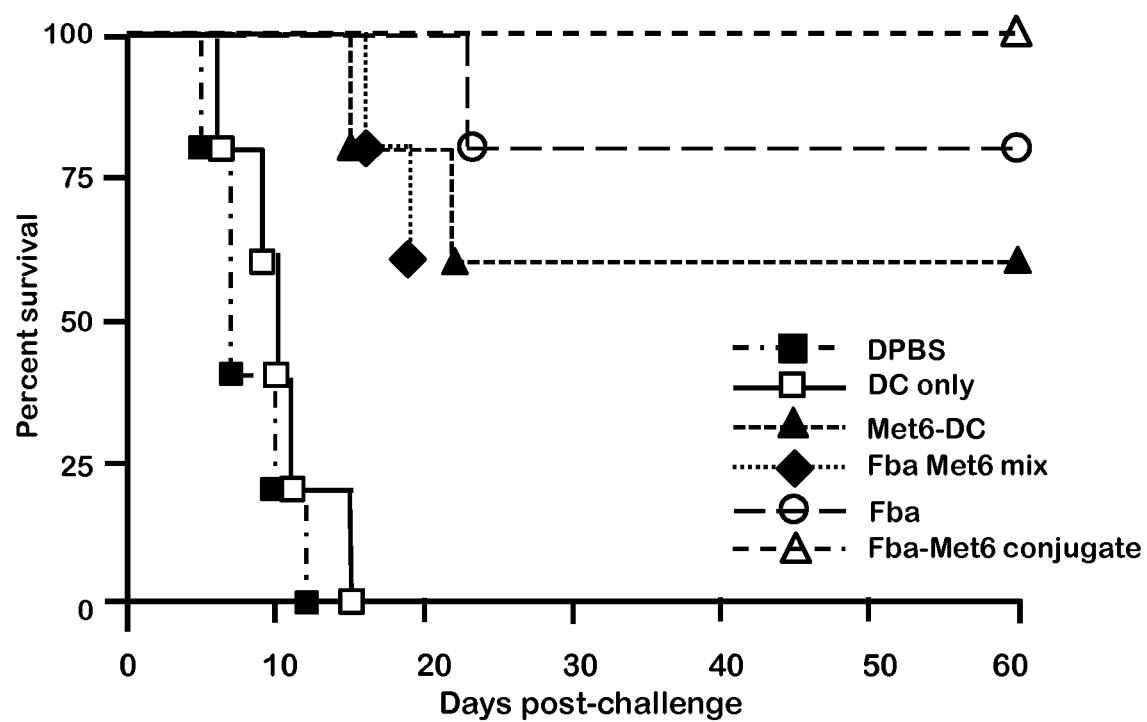
FIG. 4A depicts survival rates as a function of time for the different groups, in an experiment designed to compare the protective efficacy of the chimeric double peptide vaccine versus the two peptide mixture.
Figure 4B:
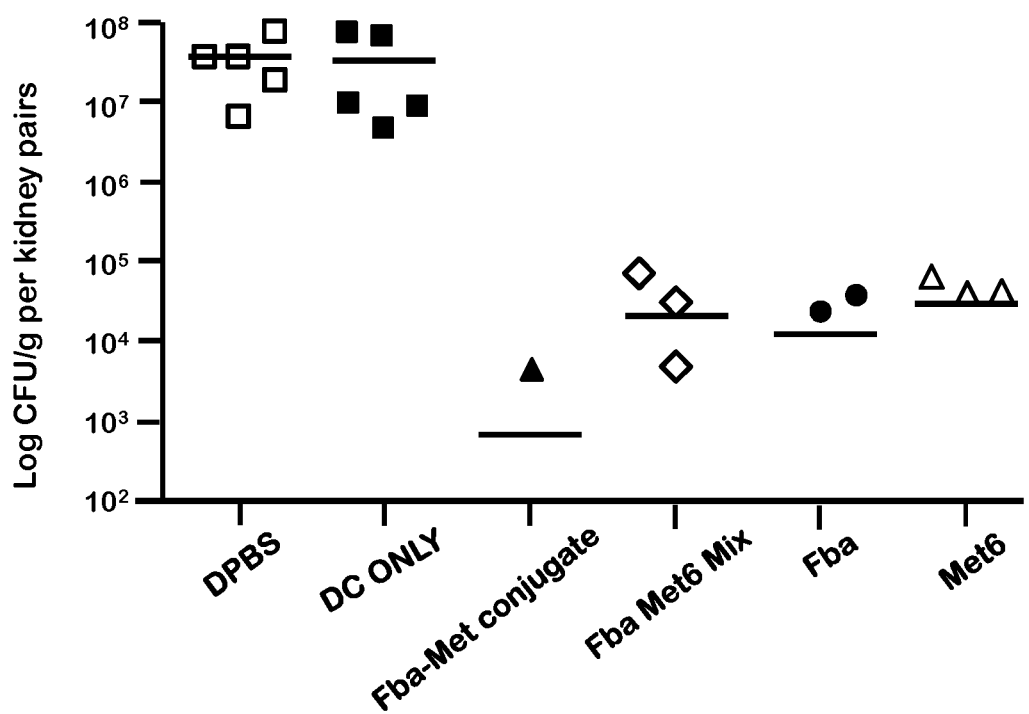
FIG. 4B depicts (on a logarithmic scale) the observed CFUs levels in the kidneys for the different groups of mice.

After the animals had been immunized and challenged with a lethal dose of *Candida*, the degree of protection was observed in all groups of immunized mice (FIG. 4A). In addition to prolonged survival times, the immunized groups had reduced or non-detectable kidney CFUs as compared to non-immune mice (FIG. 4B). Impressively, and quite surprisingly in view of the earlier, modest results with the two peptide mixture, the Fba-Met6 chimeric double peptide vaccine induced 100% complete protection up to 60 days (at the end of the experiment). Furthermore, only one mouse in that group exhibited any detectable kidney CFUs, and that one mouse had a low level of kidney CFUs. The Fba-Met6 chimeric double peptide vaccine was superior as a vaccine over the Fba peptide alone, over the Met6 peptide alone, and even over a mixture of the Fba and Met6 peptides.

FIG. 4A depicts survival rates as a function of time for the different groups. All immunized groups showed higher survival rates than were seen in the negative controls. The Fba-Met6 chimeric vaccine induced 100% complete protection up to 60 days. FIG. 4B depicts (on a logarithmic scale) the observed kidney CFU levels for the different groups of mice. The immunized mice had greatly reduced or non-detectable kidney CFUs.

The peptide-pulsed DC method was used to immunize mice in the experiments described above. Small peptides are usually degraded rapidly once injected into the body, unless they are bound to a carrier molecule such as tetanus toxoid (TT) or diphtheria toxoid (DT). The peptide-pulsed DC method could, in principle, also be used in humans. However, due to the high cost and complexity of the procedure, as a practical matter any use of the DC method in humans would likely be limited. A preferred vaccine for use in humans would therefore include the Fba-Met6 double peptide chimera, with a linker, and a carrier molecule such as TT or DT. Such preferred embodiments include, for example, Fba-KK-Met6-TT and Fba-KK-Met6-DT. Alternatively, the carrier molecule itself might also act as a linker, e.g., Fba-TT-Met6, or Met6-DT-Fba; in such a case, the peptides should be bound to the linker in a manner that preserves the peptides' immunogenicity.

We also tested each individual peptide vaccine, and the chimeric double peptide conjugate in C57BL/6 mice, which tend to generate stronger Th1 responses than do BALB/c mice. Similar results were seen in the C57BL/6 mice (data not shown).

A combination of IgG3 MAb (M2-4) and IgM MAb (E2-9) conferred enhanced protection against systemic Candidiasis in passive transfer experiments A monoclonal antibody (isotype IgG3, designated "M2-4") specific for Met6 peptide was prepared by standard hybridoma techniques. A monoclonal antibody provides the possibility of an unlimited supply of protective antibody for in vivo applications. MAb M2-4 was initially detected by an indirect immunofluorescence antibody test to confirm its specific reactivity with the Met6 peptide on the C. albicans cell surface (data not shown). BALB/c mice were given an i.p dose of MAb M2-4 four hours before hematogenous challenge with a lethal dose of C. albicans 3153A. Positive control was the IgM MAb E2-9, which is specific for Fba peptide, and whose isolation is described in Xin, H., and J. E. Cutler. 2011. Vaccine and monoclonal antibody that enhance mouse resistance to candidiasis. Clin. Vaccine Immunol. 18: 1656-1667.

Mice receiving either MAb M2-4 or MAb E2-9 showed prolonged survival as compared to negative control animals receiving either DPBS vehicle, or adsorbed MAbs. See FIG. 5A. Surprisingly, a combined treatment with both the M2-4 and the E2-9 antibodies completely protected the naive mice (100% survival). Further, the group receiving both antibodies had the lowest kidney CFUs among all the groups. See FIG. 5B.

To test the number of doses of each MAb needed to completely protect naïve mice, each MAb was administered to naïve mice every other day post challenge for two weeks. Interestingly, when either MAb M2-4 or E2-9 was given only once, either MAb provided 60% protection to the recipient animals. However, when either MAb was given every other day for two weeks, the protection from M2-4 increased to 80%, and the protection from E2-9 increased to 100%. Repeated treatment with E2-9 over a two-week period eventually produced the same level of protection as that provided by giving the two-MAb combination only once (data not shown). The combination of the two protective MAbs is preferred, as a reduced dose of MAb is required.

Figure 5A:
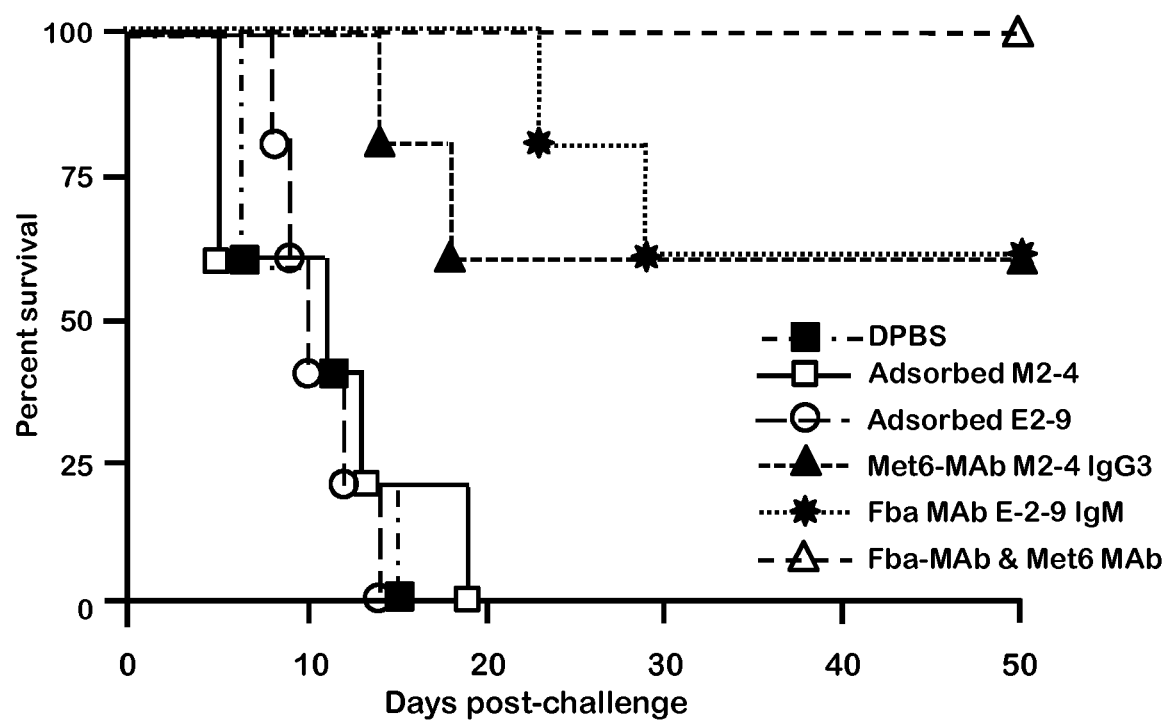
FIG. 5A depicts survival rates following lethal *C. albicans* challenge for mice given various types of passive immunization.
Figure 5B:
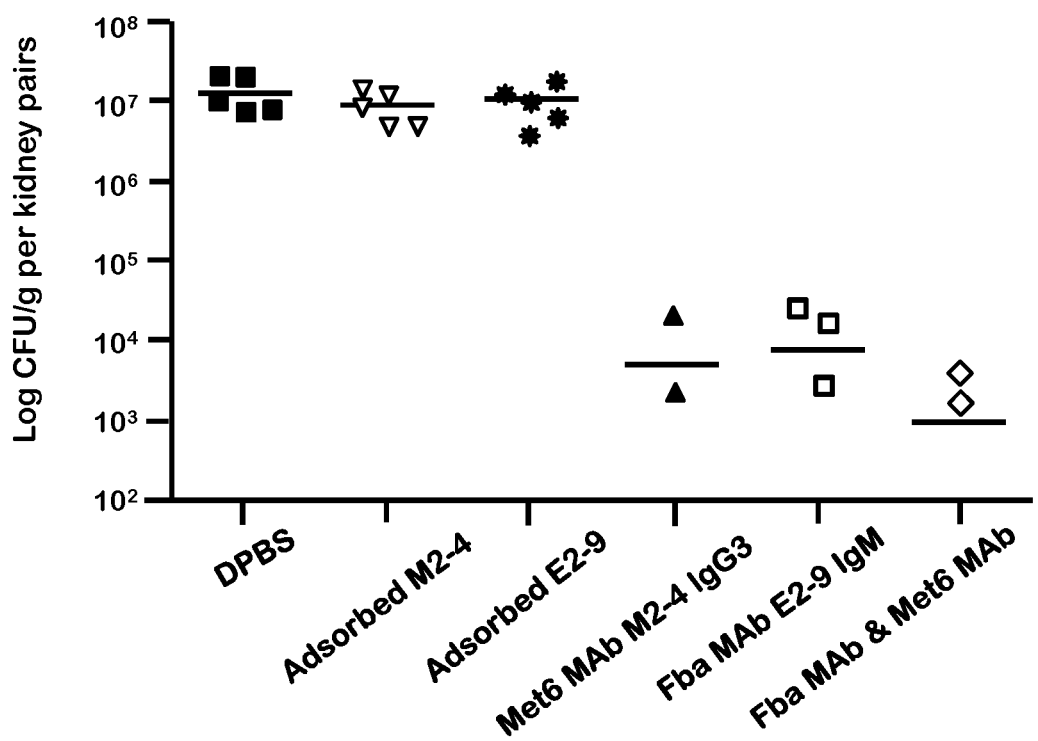
FIG. 5B depicts kidney CFU levels for mice given various types of passive immunization.

In all the transfer experiments, passive protection was prevented by removal of the MAbs through absorption with C. albicans cells before transfer (see FIGS. 5A and 5B), providing strong additional evidence for the conclusion that protection resulted from the MAbs. FIG. 5—MAbs M2-4 and E2-9 in combination conferred best protection against systemic candidiasis in passive transfer experiments.

FIG. 5A depicts survival rates following lethal C. albicans challenge for mice given various types of passive immunization. FIG. 5B depicts kidney CFU levels for mice given various types of passive immunization. The group receiving the two MAb combination had the lowest CFUs among all the groups ($P<0.01$).

Also contemplated within the scope of this invention are modifications to the antibodies to enhance their therapeutic value, or to decrease their own immunogenicity, or both. Such techniques are known in the art and include, for example, isolating the Fab receptor, "humanizing" the mouse monoclonal antibodies to produce human antibody molecules that contain one or more of the complementary determining regions (CDRs) from the mouse antibody, converting the isotype to IgG1, and the like. See, e.g., P. Chames et al., "Therapeutic antibodies: successes, limitations, and hopes for the future," Brit. J. Pharm., vol. 157, pp. 220-233 (2009); and V. Irani et al., "Molecular properties of human IgG subclasses and their implications for designing therapeutic monoclonal antibodies against infectious diseases," Mol. Immunol. (in press, 2015); U.S. Pat. No. 6,054,297.

Also contemplated within the scope of this invention are chimeric monoclonal antibodies and humanized chimeric monoclonal antibodies. A chimeric antibody is one created, for example, by substituting the mouse Fc region of the antibody molecule with the human Fc region. In a humanized chimera, the chimeric antibody is further humanized by the selective alteration of the sequence of amino acids in the Fab portion (not the CDR) of the molecule. The process is "selective" in that it does not alter the specificity of the CDR region. Aside from the CDR segments, any portions of the Fab sequence that differ from the human sequence may be exchanged with the appropriate amino acids to be more human-like.

The complete disclosures of all references cited in this specification are hereby incorporated by reference. Also incorporated by reference is the complete disclosure of the priority application, U.S. provisional application 62/016, 693. In the event of an otherwise irreconcilable conflict, however, the present specification shall control.

What is claimed:

1. A peptide comprising both an Fba domain whose amino acid sequence comprises SEQ ID NO: 1, and a Met6 domain whose amino acid sequence comprises SEQ ID NO: 2, wherein said Fba domain is covalently linked to said Met6 domain; and wherein the amino acid sequence of said peptide comprises any of SEQ ID NO: 3 through SEQ ID NO: 26.

2. The peptide of claim 1, additionally comprising a protein carrier covalently linked to said peptide.

3. The peptide of claim 2, wherein said protein carrier is tetanus toxoid or diphtheria toxoid.

4. The peptide of claim 1, wherein the amino acid sequence of said peptide comprises SEQ ID NO: 3.

5. The peptide of claim 1, wherein one or more amino acids are methylated.

6. The peptide of claim 1, wherein the peptide additionally comprises at least two cysteine residues; wherein said cysteine residues may be located inside or outside the Fba domain, the Met6 domain, or both.

* * * * *